United States Patent [19]

Daluge

[11] Patent Number: 5,087,697

[45] Date of Patent: Feb. 11, 1992

[54] THERAPEUTIC NUCLEOSIDES

[75] Inventor: Susan M. Daluge, Chapel Hill, N.C.

[73] Assignee: Burroughs Wellcome Co., Research Triangle Park, N.C.

[21] Appl. No.: 630,129

[22] Filed: Dec. 19, 1990

Related U.S. Application Data

[63] Continuation-in-part of Ser. No. 455,201, Dec. 22, 1989, which is a continuation-in-part of Ser. No. 371,870, Jun. 26, 1989, abandoned.

[30] Foreign Application Priority Data

Jun. 27, 1988 [GB] United Kingdom ............... 8815265

[51] Int. Cl.$^5$ .................... A61K 31/52; C07D 473/00; C07D 239/02
[52] U.S. Cl. ................................ 544/323; 544/244; 544/277; 544/320
[58] Field of Search ............................ 544/320, 323

[56] References Cited

FOREIGN PATENT DOCUMENTS

0349242 A2 1/1990
0424064 A1 1/1990 European Pat. Off.

OTHER PUBLICATIONS

Yoshikawa, et al., Bulletin, Chem. Soc., Japan, vol. 42, No. 12, 1969, pp. 3505–3508, Studies of Phosphorylation. III. Selective Phosphorylation of Unprotected Nucleosides.

Hoard, et al., J. Amer. Chem. Soc., vol. 87, No. 8, Apr. 20, 1965, pp. 1785–1788, Conversion of Mono- and Oligodeoxyribonucleotides of 5'-Triphosphates.

Shuto, et al., Chem. Pharm. Bulletin, vol. 36, No. 12, 1988, pp. 5020–5023, Phospholipase D-Catalyzed Trans-Alkylphosphorylation: A Facile One-Step Synthesis of Nucleoside 5'-Alkylphosphates.

Shuto, et al., Tetrahedron Letters, vol. 28, No. 2, 1987, pp. 199–202, A Facile One-Step Synthesis of 5'-Phosphatidylnucleosides by an Enzymatic Two-Phase Reaction.

Rosowsky, et al., Nucleic Acid Chemistry, Part 3, Editors: L. B. Townsend & R. S. Tipson, 1986, pp. 255–258, Alkyl Esters of 9-(5-O-Phosphone-$\beta$-D-Arabinofuranosyl)-Adenine.

Davoll, et al., J. Chem. Soc., 1960, pp. 5041–5049, The Synthesis of 9-Glycitylpurines, 3-Glycityl-[1,2,3]--triazolo[d]-pyrimidines, 8-Glycitylpteridines, and 10--Glycitylbenzo[g]pteridines, including Riboflavin and Riboflavin 2-Imine.

Bencini, et al., Analytical Biochemistry, vol. 132, 1983, pp. 254–258, Linear One-Step Assay for the Determination of Orthophosphate.

Sells, et al., Proc. Natl. Acad. Sci. USA, vol. 84, Feb. 1987, pp. 1005–1009, Production of Hepatitis B Virus Particles in Hep G2 Cells Transfected with Cloned Hepatitis B Virus DNA.

E. M. Southern, J. Biol., vol. 98, 1975, pp. 503–517, Detection of Specific Sequences Among DNA Fragments Separated by Gel Electrophoresis.

Vince et al., Antional Research 9, 120 (1988).

M. Yoshikawa et al., Bulletin Chem. Soc. Japan 1969, 42, 3505.

Primary Examiner—Cecilia Shen
Attorney, Agent, or Firm—Donald Brown; Lawrence A. Nielsen; Hannah O. Green

[57] ABSTRACT

The present invention relates to 6-substituted purine carbocyclic nucleosides and their use in medical therapy particularly in the treatment of HIV and HBV infections. The invention also relates to pharmaceutical formulations and processes for the preparation of compounds according to the invention.

9 Claims, No Drawings

THERAPEUTIC NUCLEOSIDES

This is a continuation-in-part of application Ser. No. 455,201 filed Dec. 22, 1989 which is a continuation-in-part of Ser. No. 371,870 filed June 26, 1989 now abandoned.

The present invention relates to purine nucleoside analogues containing an unsaturated carbocyclic ring in place of the sugar residue, pharmaceutically acceptable derivatives thereof, and their use in medical therapy, particularly for the treatment of certain viral infections.

AIDS (acquired immunodeficiency syndrome) is an immunosupressive or immunodestructive disease that predisposes subjects to fatal opportunistic infections. Characteristically, AIDS is associated with a progressive depletion of T-cells, especially the helper-inducer subset bearing the $OKT^4$ surface marker.

Human immodeficiency virus (HIV) has been reproducibly isolated from patients with AIDS or with the symptoms that precede AIDS. HIV is cytopathic and appears to preferentially infect and destroy T-cells bearing the $OKT^4$ marker, and it is now generally recognized that HIV is the etiological agent of AIDS.

Since the discovery that HIV is the etiological agent of AIDS, numerous proposals have been made for anti-HIV chemotherapeutic agents that may be effective in treating AIDS sufferers. Thus, for example, U.S. Pat. No. 4,724,232 describes 3'-azido-3'-deoxythymidine (which has the approved name zidovudine), its pharmaceutically acceptable derivatives and their use in the treatment of human retrovirus infections including AIDS and associated clinical conditions. Vince et al., *Antiviral Research*, 9 (½), 120 (1988) describes certain carbocyclic nucleoside analogs and their use against HIV. At the Second International Conference on Antiviral Research, Williamsburg, Va., Apr. 10–14, 1988, (±)-9-(cis-4-(hydroxymethyl)-2-cyclopentenyl) guanine (NSC-614846), also known as carbovir, was disclosed.

Worldwide, hepatitis B virus (HBV) is another viral pathogen of major consequence. It is most common in Asian countries, and prevalent in sub-Saharan Africa. The virus is etiologically associated with primary hepatocellular carcinoma.

The United States currently contains an estimated pool of 500,000-1 million infectious carriers. Chronic active hepatitis will develop in over 25% of carriers, and often progresses to cirrhosis. It is estimated that 5000 people die from HBV-related cirrhosis each year in the USA, and that perhaps 1000 die from HBV-related liver cancer. Even when a universal HBV vaccine is in place, the need for effective anti-HBV compounds will continue. The large reservoir of persistently infected carriers, estimated at 220 million worldwide, will receive no benefit from vaccination and will continue at high risk for HBV-induced liver disease. This carrier population serves as the source of infection of susceptible individuals perpetuating the incidence of disease particularly in endemic areas or high risk groups such as IV drug abusers and homosexuals. Thus, there is a great need for effective antiviral agents, both to control the chronic infection and reduce progression to hepatocellular carcinoma.

Clinical effects of infection with the HBV virus range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above.

European Patent Specification No. 349242 discloses certain 6-substituted purine carbocyclic nucleosides and their use in medical therapy particularly in the treatment of HIV and HBV infections. Among such nucleosides are the compounds (±)-cis-4-[2-amino-6-(cyclo propylamino)-9H-purin-9-yl]-2-cyclopentene-1-methanol and (±)-cis-4-[2-amino-6-(cyclopropylmethylamino)-9H-purin-9-yl]-2-cyclopentene-1-methanol, i.e. each in the form of a racemic mixture of their relevant enantiomers.

We have now found that the individual isolated enantiomers of the two compounds mentioned above and their pharmaceutical derivatives have advantageous antiviral activity, particularly against HIV and HBV infections, coupled with low cytotoxicity and/or are useful as intermediates for the preparation of compounds having such activity.

According to one feature of the present invention there are provided enantiomeric compounds of the general formula

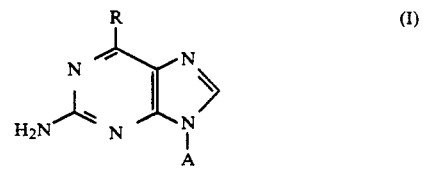

(wherein R represents a cyclopropylamino or N-cyclopropyl-N-methyl amino group and A represents the 2-cyclopentene-1-methanol-4-yl group in either the (1S,4R) or (1R,4S) configuration) and their derivatives (for example, esters, salts and salts of esters), the said compounds and their derivatives each being in the form of an enantiomer substantially free (for example to the extent of less than 10% w/w, preferably less than 5% w/w) of the corresponding enantiomer.

It will be appreciated that the compounds of formula (I) comprise the compounds having the following configurations:

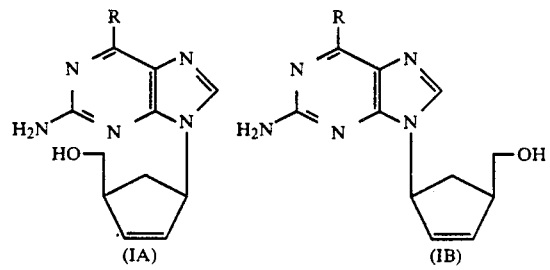

(wherein R is as defined above).

The enantiomeric compounds of formula (I), i.e. substantially free of the corresponding enantiomer, thus comprise:

1) (1S,4R)-cis-4-[2-amino-6-(cyclopropylamino)-9H-purin-9-yl]-2-cyclopentene-1-methanol
2) (1R,4S)-cis-4-[2-amino-6-(cyclopropylamino)-9H-purin-9-yl]-2-cyclopentene-1-methanol
3) (1S,4R)-cis-4-[2-amino-6-(N-cyclopropyl-N-methylamino)-9H-purin-9-yl]-2-cyclopentene-1-methanol 4) (1R,4S)-cis-4-[2-amino-6-(N-cyclopropyl-N-methylamino)-9-H-purin-9-yl]-2-cyclopentene-1-methanol Compounds 1) and 3) above, hereinafter referred to as the (1S,4R) enantiomeric compounds of formula (I), with a negative (−) optical rotation, have been found to have especially potent activity against HIV and HBV infections, and these compounds and their pharmaceutically acceptable derivatives represent preferred embodiments of the present invention. The compounds have the further advantage that, upon administration, they are capable of penetrating the blood-brain barrier to provide high levels of the compounds or active metabolites thereof in the central nervous system where manifestations of HIV infections are particularly debilitating. Compound 1) above is especially preferred in view of its exceptionally potent activity against HIV and HBV infections. The compound has also been found to have significantly lower toxicity against bone marrow progenitor cells that 3'-azido-3'-deoxythymidine (zidovudine) referred to above.

We have further found that phosphate derivatives of compounds 2) and 4) above, hereinafter referred to as the (1R,4S) enantiomeric compounds of formula (I), with a positive (+) optical rotation, have potent activity against viral infections such as those referred to above. These phosphate derivatives thus represent a further preferred embodiment of the present invention.

The reference herein to "phosphate derivatives" of the (1R, 4S) enantiomeric compounds of formula (I) denotes derivatives in which a phosphate grouping is attached to the 1-methanol group of formula (I) and includes mono-, di- and tri-phosphates.

The parent (1R,4S) enantiomeric compounds of formula (I) and non-phosphate derivatives thereof are useful as intermediates for the preparation of the said phosphate derivatives.

The above (1S, 4R) enantiomeric compounds of formula (I) and their pharmaceutically acceptable derivatives, and the phosphate derivatives of the (1R, 4S) enantiomeric compounds of formula (I), are hereinafter referred to as the antiviral compounds according to the invention.

According to further features of the present invention we provide:

a) antiviral compounds according to the invention for use in medical therapy particularly for the treatment of a retroviral infection or a hepatitis B viral infection; b) a method for the treatment of retroviral infections and hepatitis B infections in a subject, e.g. a mammal such as a human, which comprises treating the subject with a therapeutically effective amount of an antiviral compound according to the invention; and c) use of an antiviral compound according to the invention in the manufacture of a medicament for the treatment of any of the above-mentioned infections or conditions.

Examples of retroviral infections which may be treated in accordance with the invention include human retroviral infections such as human immodeficiency virus (HIV), HIV-1, HIV-2 and human T-cell lymphotropic virus (HLTV), e.g. HTLV-I or HTLV-II infections. The antiviral compounds according to the invention are especially useful for the treatment of AIDS and related clinical conditions such as AIDS-related complex (ARC), progressive generalised lymphadenopathy (PGL), AIDS-related neurological conditions, such as multiple sclerosis or tropical paraparesis, and anti-HIV antibody-positive and HIV-positive conditions for example in asymptomatic patients, and thrombocytopenic purpura. The compounds may also be used in the treatment or prevention of psoriasis.

By "a pharmaceutically acceptable derivative" in relation to the (1S,4R) enantiomeric compounds of formula (I) is meant any pharmaceutically acceptable salt, ester or salt of such ester, of a (1S, 4R) enantiomeric compounds of formula (I), or any other compound which, upon administration to the recipient, is capable of providing (directly or indirectly) such an enantiomeric compound, or an antivirally active metabolite or residue thereof.

Preferred esters of the (1S,4R) enantiomeric compounds of formula (I) include carboxylic acid esters in which the non-carbonyl moiety of the ester grouping is selected from straight or branched chain alkyl, e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulfonate esters such as alkyl- or aralkylsulfonyl (e.g. methanesulfonyl); amino acid esters (e.g. L-valyl or L-isoleucyl); and mono-, di- or tri-phosphate esters.

The phosphate esters of compounds of formula (I), may be further esterified by, for example, a $C_{1-20}$ alcohol or reactive derivative thereof, or by a 2,3-di($C_{6-24}$)acyl glycerol, for example 2,3-bis-(hexanoyloxy)propyl hydrogen phosphate and 2,3-bits-(hexadecan yloxy)propyl hydrogen phosphate derivatives. In addition to such further esterified phosphate derivatives of the compounds of formula (I), the present invention further includes such derivatives of the racemic compounds of formula (I).

With regard to the above-described esters, unless otherwise specified, any alkyl moiety present advantageously contains 1 to 18 carbon atoms, particularly 1 to 4 carbon atoms. Any aryl moiety present in such esters advantageously comprises a phenyl group.

Pharmaceutically acceptable acid addition salts of the (1S,4R) enantiomeric compounds of formula (I) include mono- or di- basic salts with the appropriate acid for example organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. The hydrochloric acid salts (i.e. the mono-and di-hydrochlorides) are particularly preferred.

The above antiviral compounds according to the invention may be employed in combination with other therapeutic agents for the treatment of the above infections or condition. Examples of such further therapeutic agents include agents that are effective for the treatment of viral infections or associated conditions such as 3'-azido-3'-deoxythymidine (zidovudine), 2',3'-dideoxynucleosides such as 2',3'-dideoxycytidine, 2',3'-dideoxyadenoside and 2',3'-dideoxyinosine, acyclic nucleosides (e.g. acyclovir), interferons such as α-interferon, renal excretion inhibitors such as probenicid, nucleoside transport inhibitors such as dipyridamole, dilazep, mio-, lido- or soluflazine, or hexobendine, immunomodulators such as interleukin II and granulocyte macrophage colony stimulating factors, soluble $CD_4$ or genetically engineered derivatives thereof, and phosphonoformic acid. The component compounds of such combination therapy may be administered simultaneously, in either separate or combined formulations, or at different times, e.g. sequentially such that a combined effect is achieved.

The antiviral compounds according to the invention, also referred to herein as the active ingredient(s), may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose for each of the above-mentioned conditions (e.g. AIDS) will be in the range of 3.0 to 120 mg per kilogram body weight of the recipient (e.g. a human) per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active compound of from about 1 to about 75 $\mu M$, preferably about 2 to 50 $\mu M$, most preferably about 3 to 30 $\mu M$. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with at least one pharmaceutically acceptable carrier or excipient. Formulations include those adapted for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention adapted for oral administration may be presented as discrete units such as capsules or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations adapted for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations adapted for rectal administration may be presented as a suppository with a suitable base comprising for example cocoa butter or a salicylate.

Formulations adapted for vaginal administration may be presented as pessaries, tampons, creams, gels, pastes, foams or spray formulations containing in addition to the active ingredient such carriers as are known in the art to be appropriate.

Formulations adapted for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be present in unit-dose or multidose sealed containers, for example, ampules and vials, and may be stored in a freeze-dried (lyophilized) condition requiring only the addition of the sterile liquid carrier, for example water for injections, immediately, prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes the following process for the preparation of enantiomeric compounds of formula (I) above and derivatives thereof. The enantiomeric starting materials and precursors for such materials which are employed as described below in relation to the process are each in the form of an anantiomer substantially free (e.g. to the extent referred to above in relation to compounds of formula (I) of the other enantiomer. The process according to the invention comprises either:

A) treating an enantiomeric compound of formula (II):

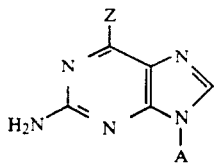

(wherein A is as hereinbefore defined and Z represents a precursor group for the said R group as defined in formula (I)) or a derivative thereof with an agent or under conditions serving to convert the precursor Z group to the desired R group; or B) reacting an enantiomeric compound of formula (III):

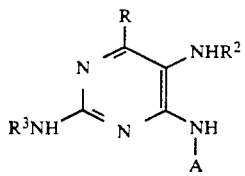

(wherein A and R are as hereinbefore defined, $R^2$ represents hydrogen or a formyl group and $R^3$ represents as amino protecting group, e.g. an acyl group such as a $C_{1-6}$ alkanoyl group, e.g. formyl, acetyl or isobutyryl) or a derivative thereof with an agent serving to effect formation of the imidazole ring in the desired compound of formula (I) followed by removal of the $R^3$ amino protecting group; or C) reacting an enantiomeric compound of formula (IV):

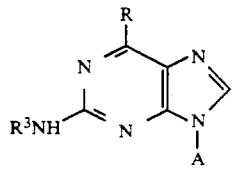

(wherein A and R are as hereinbefore defined and $R^3$ is an amino protecting group, e.g. as described above in relation to formula (III)) or a derivative thereof with an agent serving to effect removal of the $R^3$ amino protecting group, and optionally effecting one or both of the following conversions in any desired order:
i) where a compound of formula (I) is formed, converting the said compound to a derivative thereof; or
II) where a derivative of a compound of formula (I) is formed, converting the said derivative to the parent compound of formula (I) or to a further such derivative.

Process A) may be carried out in conventional manner, for example, by treatment of a compound of formula (II) in which Z represents a leaving group (e.g. a halo such as a chloro group) with an appropriate amine, i.e. cyclopropylamine or N-cyclopropyl-N-methylamine, preferably in an excess to introduce the amino R group as defined above, advantageously at reflux or at a temperature greater than 50° C., preferably in the presence of an organic solvent, for example methanol or ethanol.

Process B) may be carried out, for example, by reacting a compound of formula (III) with formic acid or a reactive formic acid derivative (e.g. triethylorthoformate or diethoxymethyl acetate) optionally with a co-solvent such as dimethylacetamide or dimethylformamide at an elevated temperature, preferably at 75°-90° C. This reaction is conveniently effected by the addition of slightly more than one equivalent of a strong anhydrous acid, e.g. with 1.1 equivalents of ethanesulfonic acid per equivalent of compound of formula (III), in which case lower temperatures (e.g. 25° C. ) are used.

Process C) may be carried out, for example, by reacting an enantiomeric compound of formula (IV) with an acidic agent, for example, dilute aqueous hydrochloric acid.

The compounds of formula (II) employed as starting materials in process A) may be prepared for example, in an analogous manner to process B), i.e. by reacting a corresponding enantiomeric compound of formula (V)

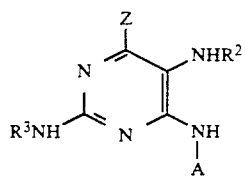

(wherein A, Z, $R^2$ and $R^3$ are as hereinbefore defined) or a derivative thereof with an agent serving to effect formation of the imidazole ring in the desired compound of formula (II) and to effect removal of the $R^3$ amino protecting group. The reaction may be carried out using those agents and conditions described above for process B).

The compounds of formula (III) employed as starting materials in process B) may be prepared for example by treating an enantiomeric compound of formula (V) above with an agent or conditions serving to convert the precursor group Z to the desired R group, in an analogous manner to that described for process A).

The compounds of formula (IV) referred to above may be prepared, for example, by reacting an enantiomeric compound of formula (VI)

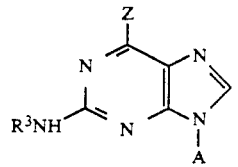

(wherein A, Z and $R^3$ are hereinbefore defined) with an agent or under conditions serving to convert the precursor group Z to the desired R group, i.e. in an analogous manner to that described for process A).

The compounds of formula (VI) above may be prepared for example by reacting an enantiomeric compound of formula (V) above with an agent serving to effect formation of the imidazole ring in the desired compound of formula (VI), for example by treatment with formic acid or a reactive formic acid derivative, as described above in relation to process B).

Enantiomeric compounds of formulae (II), (III), (IV), (V) and (VI) above represent further features of the present invention, especially those in which $R^2$ represents a formyl group and/or $R^3$ represents a $C_{1-6}$ alkanoyl group, particularly acetyl or isobutyryl, and/or Z represents a halo such as a chloro group.

Particularly preferred intermediates for the preparation of (1S, 4R)-cis-4-[2-amino-6-cyclopropylamino)-9H-purin-9-yl]-2-cyclopentene-1-methanol, i.e. the preferred compound 1) above, include:

a) (1R,4S)-cis-N-[6-(cyclopropylamino)-9-(4-(hydroxymethyl)-2-cyclopenten-1-yl)-9H-purin-2-yl]isobutyramide;

b) (1R,4S)-cis-N-[4-chloro-5-formamido-6-((4-(hydroxymethyl)-2-cyclopentene-1-yl)amino)-2-pyrimidinyl]isobutyramide;

c) (1R,4S)-cis-N-[4-chloro-5-formamido-6-((4-(hydroxymethyl)-2-cyclopentene-1-yl)amino)-2-pyrimidinyl]acetamide;

d) (1S,4R)-cis-(2-amino-6-chloro-9H-purin-9-yl)-2-cyclopentene-1-methanol.

e) (1R, 4S)-cis-N-[6-chloro-9-(4-(hydroxymethyl)-2-cyclopentene-1-yl)-9H-purin-2-yl]isobutyramide.

The enantiomeric compounds of formula (V) employed as starting materials as described above may be prepared for example by reacting a compound of formula (VII)

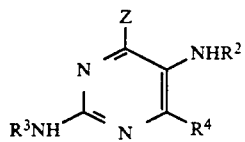
(VII)

(wherein Z, $R^2$ and $R^3$ are as hereinbefore defined and $R^4$ represents a leaving group, e.g. a halo such as a chloro group) or a derivative thereof with an enantiomeric compound of formula (VIIIA) or (VIIIB)

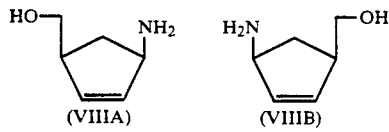

or a derivative thereof.

The last-mentioned reaction is advantageously effected in the presence of a base such as a tertiary amine for example triethylamine or trimethylamine advantageously in a organic solvent such as dimethoxyethane or ethanol.

The compounds of formula (VIIIA) or (VIIIB) having the appropriate enantiomeric configuration can be obtained by complexing the corresponding racemic compound, i.e. (±)-4-amino-2-cyclopenene-1-methanol with an optically active carboxylic acid (for example dibenzoyl-D-tartaric acid) and then fractional crystallization of resulting diastereomeric salts. Alternatively, enzymatic resolution may be employed as described for example in J. Med. Chem., 1987, 30, 745 and J. Med. Chem., 1985, 28, 1385.

The enantiomeric compounds of formula (VIIIA) or (VIIIB) and their derivatives, particularly slats thereof with optically active carboxylic acids such as dibenzoyl-D-tartaric acid, for example (1S,4R)-4-amino-2-cyclopentene-1-methanol and its dibenzoyl D tartarate represent a further feature of the present invention.

The compounds of formula (VII) employed as starting materials above may be prepared in a conventional manner for example by reducing a compound of formula (IX)

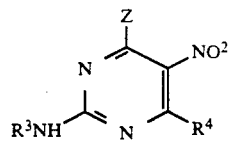
(IX)

(wherein Z, $R^3$ and $R^4$ are as hereinbefore defined) to effect conversion of the $NO_2$ group to an $NH_2$ group and optionally converting the resulting $NH_2$ group to a formamido group, for example, by treatment with formic acid/acetic anhydride.

The compounds of formula (IX) may be prepared in conventional manner. Those compounds in which Z represents a halo, for example chloro group may be prepared for example by halogenating, for example using phosphorus oxychloride, a corresponding compound of formula (X)

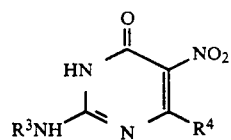
(X)

(wherein $R^3$ and $R^4$ are as hereinbefore defined).

The compounds of formula (X) may also be prepared in conventional manner, for example by reaction of a compound of formula (XI)

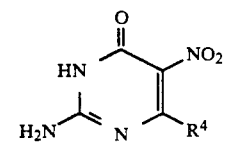
(XI)

(wherein $R^4$ is as hereinbefore defined) with an appropriate agent serving to introduce the amino protecting group, for example by reaction with an appropriate carboxylic acid or a functional equivalent thereof, e.g. isobutyric anhydride. The compound of formula (XI) may be prepared by nitration of a corresponding compound of formula (XII)

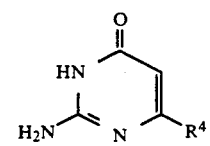
(XII)

(wherein $R^4$ is as hereinbefore defined).

The compounds of formulae (VII), (IX), (X) and (XI) represent further features of the present invention particularly those in which Z represents a halo such as a chloro group, and/or $R^3$ represents a $C_{1-6}$alkanoyl group, especially acetyl or isobutyryl, and/or $R^4$ represents a halo such as a chloro group.

Particularly preferred compounds of formulae (VII), (IX) and (X) according to the invention include:
N-(4,6-dichloro-5-formamido-2-pyrimidinyl)isobutyramide;

N-(4,6-dichloro-5-nitro-2-pyrimidinyl)isobutyramide; and

N-(4-chloro-1,6-dihydro-5-nitro-6-oxo-2-pyrimidinyl)isobutyramide.

A compound of formula (I) may generally be converted into an ester thereof by reaction with an appropriate esterifying agent, e.g. an acid halide or anhydride. The compound of formula (I), including esters thereof, may be converted into salts thereof in conventional manner, for example, by treatment with an appropriate acid. An ester or salt of a compound of formula (I) may be converted into the parent compound, for example by hydrolysis.

Thus the O-monophosphate of a compound of formula (I) may be prepared by treating the parent with an appropriate phosphorylating agent, e.g. phosphorus oxychloride as in M. Yoshikawa, T. Kato and T. Takenishi, *Bulletin Chem. Soc. Japan*, 1969, 42, 3505. The corresponding to )-di-and O- triphosphates may be prepared by methods described in "Nucleotide Analogs" K. H. Sheit, John Wiley and Sons, New York 1980, pp. 211-215, and D. E. Hoard and D. G. Ott, J. Amer. Chem. Soc. 1965, 87, 1785, e.g. by making the imidizolate derivative of the relevant O-monophosphate and by subsequent reaction of this derivative with phosphate to give O-diphosphate or with pyrophosphate to give O-triphosphate. For the preparation of esterified phosphate derivatives referred to above, the parent compound of formula (I) may be treated with an appropriate di-alkanoyl phosphatidyl choline derivative in the presence of an appropriate phospholipase for example phospholipase D, as described in S. Shuto et al., , *Tet. Lett.*, 28, 199, (1987) and *Chem. Pharm. Bull.*, 36, 5020, (1988) or by reaction of a compound of formula (I) with an appropriate phosphorylating agent such as phosphorus oxychloride followed by work-up with an appropriate alcohol as described in A. Rosowsky & S. Kin, Nucleic Acid Chemistry, Part 3, L. B. Townsend & R. S. Tipson (Editors), John Wiley & Sons, New York, 1986, 255.

The enantiomers of the compounds of formula (I) may be resolved or isolated in conventional manner, e.g. by chromatographic separation of diastereomeric esters prepared by acylation of the hydroxyl on the cyclopentenyl moiety with appropriate optically active carboxylic acid derivaties as, e.g., with naproxen (*J. Org. Chem.* 1986, 51, 1287).

The following Examples are intended for illustration only and are not intended to limit the scope of the invention in any way. In the Examples the optical rotations were assigned with respect to the sodium D line (589 nm) at 20° C. The term 'active ingredient' as used in Examples A to G means an antiviral compound according to the invention, especially compound 1) above.

EXAMPLE 1

(±)-cis-4-[(2-Amino-4-chloro-6-pyrimidinyl)amino]-2-cyclopentene-1-methanol cis-4-Acetamidocyclopent-2-enemethyl acetate [U.S. Pat. No. 4,268,672] (14.88 g, 0.073 mol) and barium hydroxide octahydrate (46.19 g, 0.146 mol) were refluxed in water (300 mL) under nitrogen for 18 hours. The resulting solution was neutralized with carbon dioxide. The precipitate was washed with water, then ethanol. The combined filtrate-wash was evaporated to a syrup (11.16 g) which was condensed with 2-amino-4,6-dichloropyrimidine (23.91 g, 0.146 mol) and triethylamine (30.5 mL, 0.219 mol) in refluxing 1-butanol (100 mL) for 1.5 hours. After addition of 1N NaOH (73 mL), the resulting mixture was evaporated to dryness and the residual solid slurried in $CHCl_2$ (200 mL). Unreacted 2-amino-4,6-dichloropyrimidine was filtered off and washed with chloroform (100 mL). The chloroform filtrate-wash was concentrated and chromatographed on a silica gel column. Additional pyrimidine starting material was eluted with 2.5% methanol-chloroform. The title compound was eluted with 3.5% methanol-chloroform as an off-white solid foam (15.90 g, 91%).

$^1$H-NMR: ($Me_2SO$-$d_6$) δ 1.15-1.28 and 2.26-2.41 (2 m, 2, $CH_2$); 2.60-2.71 (m, 1, 1'-H); 3.4 (m overlapping $H_2O$, $CH_2OH$); 4.625 (t, J=5.3, 1, $CH_2OH$); 4.95 (br s, 1, $CH-\overline{N}$); 5.67-5.87 (m, 2, $CH=CH$); 6.38 (br s, 1, $NH_2$); 7.12 (br s, 1, NH); MS (CI) M+1, 241, 243.

Anal. Calcd. for $C_{10}H_{13}N_4OCl.0.2H_2O$: C, 48.99; H, 5.55; N, 22.85; Cl, 14.46. Found: C, 49.10; H, 5,57; N, 22.81; Cl, 14.40.

EXAMPLE 2

(±)-cis-4-[[2-Amino-6-chloro-5-[(4-chlorophenyl)azo]-4-pyrimidinyl]-amino]-2-cyclopentene-1-methanol (±)-cis-4-[(2-Amino-4-chloro-6-pyrimidinyl)amino]-2-cyclopentene-1-methanol from Example 1 (11.58 g, 48.1 mmol) and sodium acetate trihydrate (97 g) were dissolved in glacial acetic acid (225 mL) and water (225 mL). A cold solution (0°-5° C.) of 4-chlorobenzenediazonium chloride was prepared form 4-chloroaniline (6.74 g, 52.8 mmol), concentrated hydrochloric acid (14.7 mL) water (52 mL), and sodium nitrite (4.01 g, 58.2 mmol in 47 mL of water). This cold solution was added dropwise over 5 minutes to the first solution. The resulting yellow precipitate was filtered after 18 hours, washed with water, and extracted with ethanol to give title compound as dark yellow powder (12.56 g, 69%), m.p. 218°-22° C. dec.

$^1$H-NMR: ($Me_2SO$-$d_6$) δ 10.25 (d, 1, NH); 7.69 and 7.54 (both, d, J=8.9, $C_6H_4$) overlapping 7.6 (br, 6, $NH_2$); 5.80-5.95 (m, 2, CH=CH); 5.24 (m, 1, CHN); 4.75 (t, 1, $CH_2OH$); 3.41 (t, 2, $CH_2OH$); 2.75 (m, 1, CH); 2.41 (m, 1, CH); 1.44-1.53 (m, 1, CH).

Anal. Calcd. for $C_{16}H_{16}N_6Cl_2O$: C, 50.67; H, 4.25; N, 22.16 Cl, 18.70. Found: C, 50.89; H, 4,29; N, 22.10; Cl, 18.66.

EXAMPLE 3

(±)-cis-4-[(2,5-Diamino-4-chloro-6-pyrimidinyl)-amino]-2-cyclopentene-1-methanol The title compound of Example 2 (11.67 g) was suspended in ethanol (235 mL), glacial acetic acid (30 mL), and water 235 mL. The mixture was heated to reflux under nitrogen. Zinc dust (13.5 g) was added in small portions over 30 minutes during which time the compound dissolved. The reaction was heated an additional 20 minutes, and then the excess zinc was filtered of from the hot solution, and it was washed with ethanol. The filtrates were evaporated, and the residue was purified on a silica gel column eluting with chloroform (1 L) and chloroform:methanol/4:1 (1.8 L). The fractions containing the product were combined, and the solvent was removed under reduced pressure to give the title compound as a red-orange oil (11.2 g, >100% yield). A pure sample was obtained during another small scale reaction to obtain the product as a light yellow solid in a 76% yield.

$^1$H-NMR: ($Me_2SO$-$d_6$) δ 1.29 and 2.39 (m, 2, $CH_2$); 2.69 (t, 1, 1'—H); 3.37 (d, 2, $CH_2OH$); 3.91 (br, 2, $NH_2$);

4.60 (br, 1, CH$_2$OH); 5.02 (m, 1, CHNH); 5.56 (br s, 2, NH$_2$); 5.74 (m, 1, =CH); 5.86 (m, 1, =CH); 6.36 (d, 1, CHNH).

EXAMPLE 4

(±)-cis-4-(2-Amino-6-chloro-9H-purin-9-yl)-2-cyclopentene-1-methanol

The title compound of Example 3 (about 9.7 g) was dissolved in diethoxymethyl acetate (100 g), and refluxed for two days. The solvent was removed under high vacuum at 50° C., and dioxane (40 mL) and 0.5N HCl (60 mL) was added. The reaction was stirred at room temperature for 1.25 hours, and then chilled. The reaction was neutralized to pH 7 with cold 5N sodium hydroxide, and then it was extracted with chloroform-methanol/3:1 several times. The organic layers were dried with magnesium sulphate, filtered, and evaporated. The residue was purified by chromatography on a silica gel column, eluting with 2% MeOH-CHCl$_3$ to give 3.7 g (46% yield) of the title compound, m.p. 138°–139° C.

$^1$H-NMR: (Me$_2$SO-d$_6$) δ 1.63 and 2.61 (m, 2, CH$_2$); 2.87 (m, 1, 1'-H); 3.44 (d, 2, CH$_2$OH); 5.44 (m, 1, CH-N); 5.89 (m, 1, =CH); 6.14 (m, 1, =CH); 6.82 (br s, 2, NH$_2$); 8.02 (s, 1, 8-H); (CH$_2$OH not seen under H$_2$O peak). UV: pH 1 λmax 315 (ξ 7370); 218 (26200); λ sh MS (EI) 265,267 (m) (CI) 266,268 (m+1).

Anal. Calcd. for C$_{11}$H$_{12}$N$_5$ClO.2H$_2$O: C, 43.79, H, 5.35; N, 23.21; Cl, 11,75. Found: C, 43.67; H, 5.29; N, 23.05; Cl, 11.70.

EXAMPLE 5

(±)-cis-4-[2-Amino-6-(cyclopropylamino)-9H-purine-9-yl]-2-cyclopentene-1-methanol The title compound of Example 4 (0.50 g) was dissolved in ethanol (40 mL), and cyclopropylamine (0.65 mL, 5 equivalent) was added. The reaction was refluxed under nitrogen for 6 hours. An additional 0.65 mL of cyclopropylamine was added, and the reaction refluxed for an additional 5.5 hours. The solvents were evaporated, and chloroform (25 mL) and saturated sodium bicarbonate solution (5 mL) was added. The aqueous layer was extracted several times with CHCl$_3$ to obtain the crude product. This was purified on a silica gel column eluting with 3% methanol-ethyl acetate to give 0.43 g (80%) of (±-cis-4-[2-amino-6-(cyclopropylamino)-9H-purin-9-yl]-2-cyclopentene-1-methanol. This was recrystallized from acetonitrile to give 0.30 g of white powder; m.p. collapses at 93°–130° C.; melts at 165° C.

$^1$H-NMR: (Me$_2$SO-d$_6$) δ 0.56 and 0.63 (2, 4, 2-cyclopropyl CH$_2$); 1.56 and 2.60 (2, 2, cyclopentenyl-CH$_2$); 2.85 (m, 1, 1'-H): 3.02 (m, 1, cyclopropyl CH-NH); 3.43 (m, 2, CH$_2$OH); 4.71 (t, 1, CH$_2$OH); 5.40 (m, 1, 4'-H); 5.77 (s, 2, NH$_2$), overlapping 5.84 (m, 1, =CH$_2$); 6.09 (m, 1, =CH); 7.23 (d, 1, NH—CH); 7.58 (s, 1, purine-8-H); ms (CI) 287 (m+1). UV: pH 1: λmax 296 (ξ 14000), 255 (10700); pH 7.0: λmax 284 (15900); 259 (9200); pH 13 λmax 284 (15800), 259 (9100).

Anal. Calcd. for C$_{14}$H$_{18}$N$_6$O.0.25H$_2$O: C, 57.82; H, 6.41; N, 28.90. Found: C, 57.84; H, 6.45; N, 28.86.

EXAMPLE 6

(±)-cis-4-(2-Amino-6-(cyclopropylmethylamino)-9H-purin-9yl)-2-cyclopentene-1-methanol (±)-cis-4-(2-Amino-6-chloro-9H-purin-9-yl)-2-cyclopentene-1-methanol (0.53 g, 2 mmol) form Example 4, N-methyl-N-cyclopropylamine (Karl Industries, Aurora, OH; 0.8477 g, 12 mmol) and methanol (20 mL) were placed in a Parr bomb and heated to 62° C. for 5 hours. The solution was concentrated and then diluted with ethanol before being brought to pH 12 by the addition of 1.0N NaOH. This solution was concentrated and the residue was purified by elution from a silica gel column with 3% methanol-chloroform (0.547 g, 91.2%). Crystallization of such a sample from water-ethanol yielded a white powder, m.p. 130°–131° C.

$^1$H-NMR: (Me$_2$SO-d$_6$) δ 7.61 (s, 1H, purine H-8), 6.10 (m, 1H, CH=), 5.84 (m, 1H, CH=), 5.7 (br s, 2H, NH$_2$), 5.40 (m, 1H, CHN), (br t, 1H, OH), 3.43 (m, 2H, CH$_2$OH) 3.24 (br s, 4H, CH$_3$, NCH cyclopropyl), 2.85 (m, 1H, CH), 2.66-2.57 and 1.61-1.51 (m, 2, cyclopentenyl CH$_2$), 0.90-0.65 (m, 4H, 2CH$_2$ of cyclopropyl).

Anal. Calcd. C$_{15}$H$_{20}$N$_6$O.0,5H$_2$O: C, 58.24; H, 6.84; N, 27.16. Found: C, 58.15; H, 6.86; N, 27.14.

EXAMPLE 7

(−)-cis-4-[2-Amino-6-(cyclopropylamino)-9H-purin-9-yl]-2-cyclopentene-1-methanol The title compound of Example 5 (0.600 g, 2.00 mmol) was dissolved in 1,3-dimethyl-3,4,5,6-tetrahydro-2-(1H)-pyrimidinone (Aldrich, 12 mL). Phosphoryl chloride (0.76 mL, 8.0 mmol) was added to the stirred, cooled (−10° C.) solution. After 3 minutes, cold water (100 mL) was added and the resulting solution neutralized with 3M ammonium hydroxide. The neutralized solution was diluted to 1 liter with water and applied to a 2.5×20 cm column of DEAE Sephadex A25 (Pharmacia) which had been preequilibrated with 50 mM ammonium bicarbonate. The column was first washed with 4 liters of 50 mM ammonium bicarbonate. The O-monophosphate of (±)-cis-4-[2-amino-6-(cyclopropylamino)-9H-purin-9-yl]-2-cyclopentene-1-methanol was then eluted with a 2-liter gradient of 50 to 300 mM ammonium bicarbonate. The fractions containing nucleotide (i.e. the above O-monophosphate) were evaporated to a white powder to remove ammonium bicarbonate; 71% calculated by UV absorbance; one peak by HPLC (see below). Snake venom 5'-nucleotidase (EC 3.1.3.5) from Crotalus atrox (1000 IU, Sigma) was added to 1.4 mmoles of the nucleotide dissolved in water (20 ml). The solution was incubated at 37° C. for 22 hours, at which time additional enzyme (1000 IU) was added. Incubation was continued for another 3 days. HPLC analysis (0.4×10 cm Whatman Partisisl 10 strong anion exchange column; elution with a gradient of 20 mM to 1M ammonium phosphate, pH 5.5, containing 5% methanol; UV detection at 284 nM) at this point showed that 50% of the starting nucleotide had been dephosphorylated to the parent nucleoside. This mixture was again applied to a DEAE Sephadex column of the type described above. Elultion with 4 liters of 50 mM ammonium bicarbonate gave fractions containing the title compound. Evaporation of the water left white powder. This material was further purified by chromatography on silica gel with MeOH:CHCl$_3$/1:9 to give colorless glass. The glass was solidified in acetonitrile to give (−)-cis-4-[2-amion-6-(cyclopropyl amino)-9H-purin-9-yl]-2-cyclopentene-1-methanol as white gummy solid which was dried to a solid foam at 0.5 mm Hg at 68° C. (260 mg, 86% from racemate); $^1$H-NMR in DMSO-d$_6$ and mass spectrum identical with those of the racemate (title compound of Example 5); [α]$^{20}_D$−59.7°, [α]$^{20}_{436}$ −127.8°, [α]$^{20}_{365}$−218.1°, (c=0.15, methanol).

Anal. Calcd. for C$_{14}$H$_{18}$N$_6$O·0.8H$_2$O: C, 55.91; H, 6.57; N, 27.94. Found: C, 56.05; H, 6.65; N, 27.88.

Continued elution of the last-mentioned Sephadex column with a 2-liter gradient of 50 to 300 mM ammonium bicarbonate gave the O-monophosphate (of the (+) enantiomer corresponding to the title compound) which was stable to 5'-nucleotidase; the preparation of this monophosphate is described in more detail in Example 9.

EXAMPLE 8

(−)-cis-4-[2-Amino-6-(cyclopropylamino)-9H-purin-9-yl]-2-cyclopentene-1-methanol O-monophosphate The title compound of Example 7 ((0.35 g, 1.2 mmol) was dissolved in 1,3-dimethyl-3,4,5,6-tetrahydro-2-(1H)-pyrimidinone (Aldrich, 5 mL). Phosphoryl chloride (Aldrich, 0.43 mL, 4.6 mmol) was added to the stirred, cooled (−10° C.) solution. After 3 minutes, cold water (20 mL) was added and the resulting solution neutralized with 3M ammonium hydroxide. Ion exchange chromatography as described in Example 7 gave the nucleotide as the diammonium salt after evaporation of water, white powder (95% yield, quantitated by UV); HPLC analysis as in Example 7 shows one peak; UV λmax nM (0.1M HCl):254, 297; pH 7 phosphate buffer):259, 284; (0.1M NaOH):259, 284. The base/phosphate ratio was 1.0/1.3 as determined by the method of B. Ames (*Methods in Enzymology* 8:115, 1966). $[\alpha]^{20}_D$−69.9°, $[\alpha]^{20}_{578}$−73.0°, $[\alpha]^{20}_{546}$−84.0° (c=0.52, MeOH:H$_2$O/4:1).

EXAMPLE 9

(+)-cis-4-[2-Amino-6-(cyclopropylamino)-9H-purin-9-yl]-2-cyclopenten-1-methanol O-monophosphate Elution of the DEAE Sephadex column described in Example 7 after 5'-nucleotidase incubation with a 2-liter gradient of 50 to 300 mM ammonium bicarbonate gave nucleotide-containing fractions which, after evaporation of water, gave the title compound as the diammonium salt; white powder (56% from title compound of Example 5); HPLC analysis as in Example 7 shows one peak; UV $\lambda_{max}$ nM (0.1M HCl): 254, 297; (pH 7 phosphate buffer): 259, 284; (0.1M NaOH): 259, 284. The base/phosphate ratio was 1.0/0.98. $[\alpha]^{20}_D$ +62.0°, $[\alpha]^{20}_{578}$+65.2°, $[\alpha]^{20}_{546}$+75.0°, (c=0.54, MeOH:-H$_2$O/4:1).

EXAMPLE 10

(+)-cis-4-[2-Amino-6-(cyclopropylamino)9H-purin-9-yl]-2-cyclopentene-1-methanol

The title compound of Example 9 (0.67 mmole) was dissolved in water (20 mL) and alkaline phosphatase (EC 3.1.3.1) form calf intestine (3000 IU, Boehringer Mannheim) was added. The solution was incubated at 37° C. for 19 hours, at which point HPLC analysis as described in Example 7 showed that all of the nucleotide had been dephosphorylated. The solution was evaporated to dryness and the residual solids extracted with refluxing ethanol (100 mL). The ethanol-soluble material was adsorbed on silica gel and applied to a silica gel column. Title compound was eluted with methanol:chloroform/1:9. Evaporation of an acetonitrile-ethanol solution gave white solid foam (164 mg, 79%); $^1$H-NMR in DMSO-d$_6$ and mass spectrum identical with those of the racemate (title compound of Example 5); $[\alpha]^{20}_D$+58.7°, $[\alpha]^{20}_{436}$+126.2°, $[\alpha]^{20}_{365}$217.5°, (c=0.10, methanol).

Anal. Calcd. for C$_{14}$H$_{18}$N$_6$O·0.60H$_2$O·0.15 EtOH: C, 56.49, H, 6.66; N, 27.64. Found: C, 56.60; H, 6.63; N, 27.55.

EXAMPLE 11

(−)-cis-4-[2-Amino-6-(cyclopropylmethylamino)-9H-purin-9-yl]-2-cyclopentene-1-methanol The title compound of Example 6, (200 g, 6.50 mmol) was dissolved in 1,3-dimethyl-3,4,5,6-tetrahydro-2(1H)-pryimidinone (Aldrich, 20 mL). Phosphoryl chloride (2.28 mL, 24.0 mmol) was added to the stirred, cooled (−10° C.) solution. After 3 minutes, cold water (80 mL) was added. The solution was extracted with chloroform (3×80 mL). The aqueous layer was diluted with ethanol (400 mL) and the pH adjusted to 6 with saturated aqueous NaOH. The precipitated inorganic salts were filtered off. The filtrate was further diluted with ethanol to a volume of 1 liter and the pH adjusted to 8 with additional NaOH. The resulting precipitate was filtered and dried to give the O-monophosphate of (±)-cis-4-[2-amino-6-(cyclopropylmethylamino)-9H-purin-9-yl]-2-cyclopentene-1-methanol as white powder (4.0 mmoles, 62% quantitated by UV absorbance); HPLC analysis as in Example 7 shows one peak. This racemic O-monophosphate was dissolved in water (200 mL) and snake venom 5'-nucleotidase (EC 3.1.3.5) from *Crotalus atrox* (5,000 IU, Sigma) was added. After incubation at 37° C. for 10 days, HPLC analysis as described in Example 7 showed that 50% of the starting nucleotide had been dephosphorylated to the nucleoside. These were separated on a 5×14 cm column of DEAE Sephadex A25 (Pharmacia) which had been preequilibrated with 50 mM ammonium bicarbonate. The title compound was eluted with 2 liters of 50 mM ammonium bicarbonate. Evaporation of water gave white powder which was dissolved in methanol, adsorbed on silica gel, and applied to a silica gel column. Title compound was eluted with methanol:chloroform/1:9 as a colorless glass. An acetonitrile solution was evaporated to give white solid foam, dried at 0.3 mm Hg over P$_2$O$_5$; 649 mg (72% from racemate); $^1$H-NMR in DMSO-d$_6$ and mass spectrum identical with those of the racemate (title compound of Example 6); $[\alpha]^{20}_D$−48.0°, $[\alpha]^{20}_{365}$−149° (c=0.14, methanol).

Anal. Calcd. for C$_{15}$H$_{20}$N$_6$O−0.10 CH$_3$CN: C, 59.96; H, 6.72; N, 28.06. Found: C, 59.93; H, 6.76; N, 28.03.

Continued elution of the Sephadex column with 2 liters of 100 mM ammonium bicarbonate and then with 2 liters of 200 mM ammonium bicarbonate gave O-monophosphate of the (+) enantiomer corresponding to the title compound, which was stable to 5'-nucleotidase.

EXAMPLE 12

(±)-cis-4-[2-Amino-6-(cyclopropylmethylamimo)-9H-purin-9-yl]-2-cyclo-pentene-1-methanol The fractions containing O-monophosphate of the (+) enantiomer eluted from the Sephadex column of Example 11 were combined and alkaline phosphatase (EC 3.1.3.1) from calf intestine (4800 IU, Boehringer Mannheim) was added. The solution was incubated at 25° C. for 18 hours, at which point HPLC analysis showed that all of the nucleotide has been dephosphorylated. The solution was evaporated to dryness and the residual solids extracted with refluxing ethanol (100 mL). The ethanol-soluble material was adsorbed on silica gel and applied to a silica gel column. Title compound was eluted with methanol: chloroform/1:9 as a colorless glass. An acetonitrile solution was evaporated to give white solid foam, dried at 0.3 mm Hg over $P_2O_5$; 659 mg (73% from racemate); $^1$H-NMR in DMSO-$d_6$ and mass spectrum identical with those of the racemate (title compound of Example 6); $[\alpha]^{20}_D$ +47.0°, $[\alpha]^{20}_{436}$ +93.0°, $[\alpha]^{20}_{365}$ +141.3° (c=0.11, methanol).

Anal. Calcd. for $C_{15}H_{20}N_6O$-0.1 $CH_3CN$: C, 59.95; H, 6.72; N, 28.06. Found: C, 59.92; H, 6.80; N, 27.96.

EXAMPLE 13

(1S,4R)-4-Amino-2-cyclopentene-1-methanol dibenzoyl-D-tartrate (±)-cis-4-Acetamidocyclopent-2-enemethyl acetate [U.S. Pat. No. 4,268,672] (14.88 g, 0.073 mol) and barium hydroxide octahydrate (46.19 g), 0.146 mol) were refluxed in water (300 ml) under nitrogen for 18 hours. The resulting solution was neutralised with carbon dioxide. The precipitate was washed with water, then ethanol. The combined filtrate was evaporated to a syrup, (acetic acid salt of (±)-4-amino-2-cyclopentene-1-methanol) which converted to free amine by stirring with an excess of Amberlite IRA-400 (OH$^-$) resin in water. The resin was filtered off, washed with water, and the filtrate-wash evaporated to a pale yellow syrup which was dried by evaporation of portion of ethanol. Such a sample of amine (2.26 g, 20.0 mmol) and dibenzoyl-D-tartaric acid (Aldrich, 3.62 g, 10.0 mmol as 99%) were dissolved in hot absolute ethanol (35 ml). Refluxing acetonitrile (ca. 150 ml) was added to the cloud point and the solution was allowed to cool slowly to room temperature. The white needles which formed were recrystallized three times from the same solvent combination to give title compound as white plates (1.07 g, 37%); m.p. 160°-162°; $[\alpha]_D^{20}$+66.9°, $[\alpha]_{436}^{20}$+165°, $[\alpha]_{365}^{20}$+325° (c=0.28, methanol). X-ray crystallography of this salt allowed the absolute configuration of the cation to be fixed by the known configuration of the D-dibenzoyl tartaric acid dianion. This salt crystallized in the space group $C_2$ with one $C_6H_{12}NO$ cation and one-half $C_{18}H_{14}O_8$ dianion as the asymmetric unit.

Anal. Calcd. for $C_6H_{11}NO$-½ ($C_{18}H_{14}O_8$): C, 61.63; H, 6.21; N, 4.79. Found: C, 61.56; H, 6.24; N, 4.74.

EXAMPLE 14

(1R, 4S)-4-Amino-2-cyclopentene-1-methanol dibenzoyl-L-tartrate

This salt was formed and crystallized as described in Example 13, except that dibenzoyl-L-tartaric acid was used. Three crystallizations from ethanol-acetonitrile gave the title compound as white plates (1.00 g, 34%); m.p. 160°-162°; $[\alpha]_D^{20}$−68.2°, $[\alpha]_{436}^{20}$−169°, $[\alpha]_{365}^{20}$−333°, (c=0.24, methanol).

Anal. Calcd. for $C_6H_{11}NO$-½ ($C_{18}H_{14}O_8$): C, 61.63; H, 6.21; N, 4.79. Found: C, 61.59; H, 6.21; N, 4.76.

EXAMPLE 15

(±)-cis-N-[4-chloro-5-formamido-6-[[4-(hydroxymethyl)-2-cyclopentene-1-yllamino]-2-pyrimidinyl]acetamide N-(5-Amino-4,6-dichloropyrimidin-2-yl)acetamide (J. Org. Chem. 1975, 40, 3141) was formulated by addition of 96% formic acid (20 ml) to a solution of (0.75 g, 3.4 mmoles) dissolved in acetic anhydride (20 ml). The resulting solution was stirred at 25° C. for one hour and then evaporated to give (0.77 g, 91%); structure confirmed by $^1$H-NMR and mass spectrum. This tan powder (840 mg, 3.37 mmol), (±)-cis-4-amino-2-cyclopentene-1-methanol (940 mg, 8.2 mmol), and triethylamine (0.80 g, 8.0 mmol) were warmed in ethanol (50 ml) in an oil bath (70°-80° C.) under nitrogen for 50 minutes and evaporated to a dark oil which was chromatographed on silica gel. Title compound was eluted with 5% methanol-chloroform as a peach-colored solid foam (840 mg). Crystallization from methanol gave white granules (575 mg, 52%); m.p. 189°-193°; $^1$H-NMR (DMSO-$d_6$) δ 10.23 (br, 1.0, NHAc), 9.3 (br, 1.0 NHCHO), 8.15 and 7.90 (both s, 1.0, HC=O from two conformers, peaks coalesce at 60° C.), 7.42 and 7.22 (both d, J=8.3, total 1.0, CH—NH from two conformers, peaks coalesce at 60° C.), 5.9 and 5.7 (both m, 2.0, CH=CH), 5.05 (m, 1, OH), 3.39 (m, 2, CH$_2$OH), 2.72 (m, 1, CH), 2.40 (m, 1, ½ CH$_2$), 1.36 m, 1, ½ CH$_2$).

Anal. Calcd. for $C_{13}H_{16}N_5O_3Cl$: C, 47.93; H, 4.95; N, 21.50; Cl, 10.88. Found: C, 47.99; H, 4.96; N, 21.42; Cl, 10.96.

EXAMPLE 16

(±)-cis-4-[2-Amino-6-(cyclopropylamino)-9H-purin-9-yl]-2-cyclo-pentene-1-methanol The title compound of Example 15 (0.91 g, 2.79 mmol) was dissolved in dry DMF (1 ml). Triethylorthoformate (10 ml) and ethane sulfonic acid (0.29 ml, 3.4 mmol) were added and the solution heated at 65° C. for 24 hours. The solution was evaporated to a syrup. The syrup was dissolved in 1N HCl (15 ml) and stirred for three hours. The pH was adjusted to 7 with 5N sodium hydroxide and the resulting mixture (oil formed) was extracted with i-propanol:chloroform/1:3 (3×100 ml). The combined organic layers were dried (MgSO$_4$) and evaporated to a red glass (0.93 g). A sodium of this glass in methanol (20 ml) was heated with cylcopropylamine (2 ml) in a Parr bomb at 70° C. for 18 hours. The resulting solution was evaporated to a dark glass which was adsorbed on silica gel. Elution with 7% methanol-ethylacetate gave title compound (148 mg, 19%) as white powder, after trituration with acetonitrile; $^1$H-NMR (DMSO-$d_6$) identical with that of the title compound of Example 5.

EXAMPLE 17

(±)-1R,4S)-cis-N-[4-Chloro-5-formamido-6-{[4-(hydroxymethyl)-2-cyclopentene-1-yl]amino}-2-pyrimidinyl]acetamide (1S,4R)-4-Amino-2-cyclopentene-1-methanol dibenzoyl-D-tartrate prepared as described in Example 13 (2.76 g, 9.02 mmol) was dissolved in water (20 ml) and applied to a column of 65 ml of Amberlite IA-400 (OH$^-$ form) anion exchange resin. The column was washed with water. Basic fractions were combined and evaporated to a residual oil which was dried by evaporation of absolute ethanol and then at 0.5 mm to give oil (darkens rapidly in air) which was used immediately. This oil was dissolved in ethanol (5 ml) and added to a solution of N-(4,6-dichloro-5-formamido-2-pyrimidinyl)acetamide (2.07 g, 8.31 mmol), prepared as described in Example 15, and triethylamine (2.50 g, 24.8 mmol). The resulting dark solution was heated (oil bath 75°-80° C.) under nitrogen for 50 minutes. The solution was evaporated to a syrup which was applied to a silica gel column. Title compound was eluted with 3 to 5% methanol-chloroform as a pale yellow solid foam (1.59 g, 54%); $^1$H-NMR identical with that of crystallized sample. Such a sample was crystallized from ethanol to give white granules, m.p. 194°–195° C.; $^1$H-NMR (DMSO-$d_6$) identical with that of the title compound of Example 15; $[\alpha]^{20}_D$ +2.7°, $[\alpha]_{546}^{20}$+2.9°, $[\alpha]_{436}^{20}$−2.5°, $[\alpha]_{365}^{20}$−41.2° (c=0.238, methanol).

EXAMPLE 18

(−)-(1S,4)-cis-(2-Amino-6-chloro-9H-purin-9-yl)-2-cyclopentene-1-methanol

The title compound of Example 17 (1.15 g, 3.53 mmol) was gently refluxed in diethoxylmethyl acetate (45 ml) under nitrogen for 3.5 hours. The resulting pale yellow solution was concentrated at 0.5 mm Hg to a yellow syrup. The syrup was stirred in 1N HCl (50 ml) for 1.0 hour. This solution was neutralized with sodium bicarbonate and evaporated to dryness. The residual solids were extracted with methanol and the methanol-soluble material applied to a silica gel column. Elution of the column with 10% methanol-ethyl acetate gave title compound as a pale yellow solid foam (730 mg), 78%); $^1$H-NMR (DMSO-$d_6$): identical with that of racemate (title compound of Example 4); $[\alpha]_D^{20}$−114.9° (c=0.26, MeOH).

EXAMPLE 19

(−)-(1S,4R)-cis-4-[2-Amino-6-(cyclopropylamino)-9H-purin-9-yl]-2-cyclopentene-1-methanol The title compound of Example 18 (560 mg, 2.11 mmol) in methanol (12 ml) was heated with cyclopropylamine (2.4 ml) in a Parr bomb at 78° C. for 17 hours. The solvent was evaporated and the residue chromatographed on silica gel. Title compound was eluted with 5–7% methanol-ethyl acetate as a colorless solid foam (367 mg, 59%); $^1$H-NMR (DMSO-$d_6$) identical with that of Example 7; $[\alpha]_D^{20}$−59.0° (c=0.28, MeOH) confirms the absolute configuration of the title compound of Example 7.

EXAMPLE 20

(1S,4R)-4-Amino-2-cyclopentene-1-methanol dibenzoyl-D-tartrate

2-Azabicyclo[2.2.1]hept-5-en-3-one [Daluge and Vince, J. Org. Chem. 1978, 43, 2311 and U.S. Pat. No. 4,268,672] (44.0 g, 0.400 mole) was stirred in 2N HCl in methanol (0.5 L) at 25° C. for 1.5 hours. Volatiles were evaporated to leave (±)-cis-methyl-4-amino-2-cyclopentene-1-carboxylate hydrochloride as an off-white powder (71.1 g). Trituration of such a sample with diethylether gave a white powder, m.p. 92.5°–95° C. [J. Org. Chem. 1981, 46, 3271; m.p. 82°–83° C.]; $^1$H-NMR (DMSO-$d_6$) δ 8.25 (br s, 3, NH$_3^+$), 6.1 and 5.9 (both m, 2, CH=CH), 3.64 (s) overlapping 3.75–3.6 (m, total 4, OMe and CH), 2.65–2.45 and 2.05–1.85 (both m, 2, CH$_2$).

Anal. Calcd for $C_7H_{11}NO_2$·HCl: C, 47.33; H, 6.81; N, 7.89; Cl, 19.96. Found: C, 47.41; H, 6.84; N, 7.85; Cl, 19.89.

(±)-cis-Methyl-4-amino-2-cyclopentene-1-carboxylate hydrochloride (17.7 g, 0.100 mole) and diisobutylaluminum hydride (0.500 mole as a 1M solution in hexane) were refluxed in hexane (200 ml) for 6 hours. The resulting solution was cooled and 10 ml of 1M aqueous ammonium chloride and then methanol (200 ml) were added. This mixture was refluxed for 30 minutes and MgSO$_4$ (10 g) added. Solids were filtered off and washed with additional methanol. The filtrate-wash was evaporated to a dark oil (15.5 g); $^1$H-NMR (DMSO-$d_6$) identical to that of (±)-4-amino-2-cyclopentene-1-methanol prepared as described in Example 13. Such a sample, after purification by chromatography on silica gel (EtOH:CHCl$_3$:NH$_4$OH/10:90:1) was crystallized with dibenzoyl-D-tartaric acid to form the title compound.

EXAMPLE 21 cis-4-(2-Amino-6-(cyclopropylamino)-9H-purin-9-yl)-2-cyclopenten-1-yl]methyl R-2,3-bis-(hexadecanoyloxy)propyl hydrogen phosphate A solution of L-α-dipalmitoyl phosphatidyl choline (150 mg, 0.2 mmol, Sigma) in 6 ml of chloroform was added to a flask containing (±)-cis-4-(2-amino-6-(cyclopropylamino)-9H-purin-9-yl)-2-cyclopentene-1-methanol (300 mg, 1.03 mmol), phospholipase D, Type VII (from Streptomyces, 1.0 mg, specific activity 185 units/mg, Sigma) and pH 4.5 buffer (1.5 ml, 250 mM in CaCl$_2$, 200 mM in NaOAc adjusted to pH 4.5 by addition of 0.1N HCl). The resulting biphase was stirred at 45° C. (oil bath) for 1 hour. The layers were separated and the aqueous layer extracted with chloroform (3×6 ml). The combined organic layers were washed with 1N HCl, dried and concentrated. Such a sample was purified by elution from 2 silica gel columns with 12% methanol-chloroform to yield title compound, 120 mg (47%). This material was solidified using ethylacetate-acetonitrile to produce a light yellow powder m.p. 155°–157° C.; $^1$H-NMR (CD$_3$CD-CDCl$_3$) δ 7.78 (s, overlapping solvent, purine H-8), 6.12 and 5.88 (m, 2, HC=CH), 5.53 (m, 1, CHN cyclopentene), 5.22 (m, 1, CO$_2$CH), 4.37 (dd, J=3, 12; 1, 0.5 POCH$_2$ glycerol), 4.12 (m, 1, 0.5 POCH$_2$ glycerol), 3.42 (m, 4, OCH$_2$ glycerol, OCH$_2$), 3.11 (br m, 1, CH), 2.90 (m, 1, NCH), 2.78 (m, 1, 0.5 CH$_2$ cyclopentene), 2.27 (m, 4, 2CH$_{CO2}$), 1.70 (m, 1, 0.5 CH$_2$ cyclopentene), 1.56 (br m, 4, 2CH$_2$CH$_2$CO$_2$), 1.27 (br m, 38, 24 CH$_2$), 0.88 (m, 6, 2CH$_3$), 0.83 (m, 2, CH$_2$ cyclopropyl), 0.60 (m, 2, CH$_2$ cyclopropyl).

Anal. Calcd. for $C_{49}H_{85}N_6O_8P$·2.4 H$_2$O: C, 61.28; H, 9.42; N, 8.75; P, 3.22. Found: C, 60.97; H, 9.12; N, 8.78; P, 2.96.

EXAMPLE 22

[cis-4-(2-Amino-6-(cyclopropylamino)-9H-purin-9-yl)-2-cyclopenten-1-yl]methyl R-2,3-bis-(hexanoyloxy)propyl hydrogen phosphate A solution of L-α-dicaproyl phosphatidylcholine (300 mg, 0.66 mmol, Sigma) in 15 ml of CHCl$_3$ was added to a flask containing (±)-cis-4-(2-amino-6-(cyclopropylamino)-9H-purin-9-yl)-2-cyclopentene-1-methanol (378 mg, 1.32 mmol), phospholipase D, Type VII (from Streptomyces, 1.04 mg, specific activity 185 units/mg, Sigma), pH 4.5 buffer (4.5 ml, 250 mM in CaCl$_2$, 200 mM in NaOAc adjusted to pH 4.5 with HCl) and CHCl$_3$ (3 ml). The resulting biphase was stirred at 45° C. (oil bath) for 4 hours. The layers were separated and the organic layer washed with 1N HCl (2×4 ml). The combined aqueous layers were back washed with chloroform (10 ml). The combined organic layers were dried (MgSO$_4$) and concentrated. The residue was placed on a silica gel column and the title compound was eluted with 16% methanol-chloroform and concentrated to yield a fine yellow powder. This material was dissolved in ethanol and concentrated (3×50 ml) before drying under high vacuum to yield 103 mg (21% yield) of a light yellow powder, m.p. 182°–185° C.

$^1$H-NMR: (DMSO-d$_6$) α 7.61 (s, 1, purine H8), 7.22 (br s, 1, NH), 6.09 (m, 1, 0.5 CH=CH), 5.89 (m, overlapping br s at 5.83, 3, 0.5 CH=CH, NH$_2$), 5.41 (br m, 1, CHN), 5.09 (br m, 1, CO$_2$CH), 4.30 (dd; J=2.7, 12; 1, 0.5 POCH$_2$ glycerol), 4.08 (m, 1, 0.5 POCH$_2$ glycerol), 3.80 (br m overlapping br m at 3.75, 4, OCH$_2$ glycerol, OCH$_2$), 3.02 (br m, 2, CH, NCH cyclopropropyl), 2.65 (m, 1, 0.5 CH$_2$ cyclopentene), 2.23 (+, J=7.5, 4, 2 CH$_2$CO$_2$), 1.48 (br m, 5, 2 CHCH$_2$CO$_2$, 0.5 CH$_2$ cyclopentene), 1.23 (br m, 8, 2 (CH$_2$)$_2$), 0.84 (m, 6, 2 CH$_3$), 0.67 and 0.58 (m, 4, 2 CH$_2$ cyclopropyl).

Anal. Calcd. for C$_{29}$H$_{45}$N$_6$O$_8$P·3.9 H$_2$O, 0.2 CHCl$_3$, 0.05 EtOH: C, 48.00; H, 7.33; N, 11.46; Cl, 2.9. Found: C, 48.65; H, 6.61; N, 10.81; Cl, 2.5.

The preceding example is an adaptation of the procedure by Satoshi Shuto et al. Tetrahedron Letters, Vol. 28, No. 2, pp. 199-202, 1987.

EXAMPLE 23

N-(4-Chloro-1,6-dihydro-5-nitro-6-oxo-2-pyrimidinyl)isobutyramide

6-Chloro-5-nitroisocytosine (J. Chem. Soc. 1960, 5041; J. Org. Chem. 1975, 40, 3141) was protected by heating the yellow solid (14.88 g, 78.09 mmol) to 100° C. for one hour in isobutyric anhydride (250 ml) and concentrated sulphuric acid (3–4 drops). The resulting solution was treated with anhydrous methanol (100 ml), stirred at 50° C. for half an hour, concentrated to a third of the original volume, and the title compound (14.97 g, 74%) was collected by filtration as pale yellow crystals; m.p. 196°–199° C. (dec); $^1$H-NMR (DMSO-d$_6$) δ 1.12 (d, J=6.9, Hz, 6H, (CH$_3$), 2.75 (m, J=6.9, Hz, 1H, (CH$_3$)$_2$CH), 12.41 (br s, 1H).

Anal. Calcd. for C$_8$H$_9$N$_4$O$_4$Cl: C, 36.87; H, 3.48; N, 21.50; Cl, 13.60. Found: C, 36.94; H, 3.48; N, 21.44; Cl, 13.53.

EXAMPLE 24

N-(4,6-Dichloro-5-nitro-2-pyrimidinyl)isobutyramide

The title compound of Example 23 (10.0 g, 38.37 mmol) was heated to reflux in phosphorus oxychloride oxychloride (200 ml) and N,N-diethylaniline (3–4 drops) for 5 hours under nitrogen. The solution was then cooled to room temperature, concentrated to dryness, and the syrup was dissolved in cold (~ −10° C.) methylene chloride (200 ml). The organic layer was treated with saturated aqueous sodium bicarbonate (100 ml) with vigorous stirring, and the temperature was kept below 5° C. as solid sodium bicarbonate was added portionwise to elevate the pH to between 5 and 7. The layers were separated and the aqueous phase was extracted with methylene chloride. The combined organic layers were filtered over phase-separator paper, concentrated and dried under vacuum to give the title compound (7.71 g, 72%) as a yellow-white solid sufficiently pure to employ in the next step. Recrystallisation of the solid from hexane/methylene chloride provided an analytical sample, m.p. 166°–169° C.; $^1$H-NMR (DMSO-d$_6$) δ 1.09 (d, J=6.9 Hz, 6H, (CH$_3$)$_2$CH), 2.79 (m, J=6.9 Hz, 1H, (CH$_3$)$_2$CH), 11.61 (s, 1H).

Anal. Calcd. for C$_8$H$_8$N$_4$O$_3$Cl$_2$: C, 34.43; H, 2.89; N, 20.08; Cl, 25.41. Found: C, 34.53; H, 2.89; N, 20.02; Cl, 25.40.

EXAMPLE 25

N-(4,6-Dichloro-5-formamido-2-pyrimidinyl)isobutyramide

The title compound of Example 24 (6.77 g, 24.26 mmol) was placed in a Parr bottle containing 220 ml absolute EtOH and 10.0 g (wet) Raney nickel catalyst that had been previously shaken under hydrogen (40 psi) for 10 minutes. The mixture was shaken under hydrogen (40 psi) for an hour, filtered over celite, and the filtrate was concentrated to a yellow-white solid that was dried under vacuum overnight. This solid was stirred in 1,2-dichloroethane (250 ml) at 0° C. Acetic anhydride (30 ml) was added, followed by formic acid (30 ml), dropwise under nitrogen. The resulting mixture was stirred at room temperature for 2 hours, concentrated to half the original vlume; and azeotroped with toluene to remove residual formic/acetic acid. The crude solid was triturated with methanol to give the title compound (4.92 g, 73%) as an off-white solid; m.p. 206°–209° C. (dec); $^1$H-NMR (DMSO-d$_6$) δ 1.08 (d, J=6.8 Hz, 6.0 (CH$_3$)$_2$CH), 2.74 (m, J=6.8 Hz, 1.0 (CH$_3$)$_2$CH), 8.18 (d, J=10.3 Hz) and 10.26 (br s) [total 1.0, NHCHO from two conformers], 11.17 br s, 1.0).

Anal. Calcd. for C$_9$H$_{10}$N$_4$O$_2$Cl$_2$: C, 39.01; H, 3.64; N, 20.22; Cl, 25.59. Found: C, 39.13; H, 3.68, N, 20.12; Cl, 25.67.

EXAMPLE 26

(±)-(1R,4S)-cis-N-[4-Chloro-5-formamido-6-{[4-(hydroxymethyl)-2-cyclopentene-1-yl]amino}-2-pyrimidinyl]isobutyramide.

(1S,4R)-4-Amino-2-cyclopentene-1-methanol dibenzoyl-D-tartrate (2.44 g, 8.15 mmol) prepared as described in Example 13, was dissolved in 90% ethanol (20 ml) and the solution added to a column of Amberlite IRA-400 (OH$^-$) resin (30 ml) which had been prewashed with the same solvent.

Elution with 90% ethanol gave basic fractions which on concentration and evaporation of portions of toluene-ethanol, left (1S,4R)-4-amino-2-cyclopentene-1-methanol as pale yellow oil (1.4 g) which was condensed immediately with N-(4,6-dichloro-5-formamido-2-pyrimidinyl isobutyramide (2.26 g, 8.15 mmol) prepared as described in Example 25, in 1,2-dimethoxyethane (100 ml) with triethylamine (2.3 ml, 16.3 mmol) at 95°–110° C. for 1.5 hours. The resulting solution was evaporated to a dark yellow syrup which was chromatographed on silica gel. Elution of column with 5–7.5% methanol-chloroform gave the title compound as pale yellow solid (2.45 g, 84%). Crystallisation of such a sample from acetonitrile gave the title compound as fine white crystals, mp. 194°–195.5° C.

$^1$H-NMR (DMSO-d$_6$) δ 10.21 (s, 1, NHCOCHMe$_2$), 9.29 (s, 1, NHCHO), 8.12 (s, 1, CHO), 7.18 (d, J=7.9, 1, CHNH), 5.8 and 5.7 (both m, 2, CH=CH), 5.08 (m, 1, CHN), 4.71 (t, J=5.06 1, OH), 3.37 (m, 2, CH$_2$OH); 2.9–2.6 (m,2, CHMe$_2$ and CH), 2.40 (m, 1, 0.5 CH$_2$), 1.33 (m, 1, 0.5 CH$_2$); [α]$_D^{20}$+4.4°, [α]$_{365}^{20}$−20.7° (c=0.237, MeOH).

Anal. Calcd. for C$_{15}$H$_{20}$N$_5$ClO$_3$: Calcd.: C, 50.92; H, 5.70; N, 19.79; Cl, 10.02. Found: C, 50.67; H, 5.78; N, 19.62; Cl, 9.92.

EXAMPLE 27

(−)-(1R,4S)-cis-N-(cyclopropylamino)-9-(4-hydroxymethyl)-2-cyclopentene-1-yl)-9H-purin-2-yl]isobutyramide (+)-(1R,4S)-cis-N-[4-chloro-5-formamido-6-{[4-(hydroxymethyl(-2-cyclopentene-1-yl]amino}-2-pyrimidinyl]isobutyramide (1.949 g, 5.44 mmol) prepared as described in Example 26, was stirred with triethylorthoformate (30 ml) in an ice-water bath while concentrated hydrochloric acid (2.0 ml) was added dropwise over two minutes. The resulting clear solution was stirred at ambient temperature overnight.

The volatiles were removed under vacuum and the residual syrup (containing a (1R, 4S)-cis-N-[6-chloro-9-(4-hydroxymethyl)-2-cyclopentene-1-yl)-9H-purin-2-yl]isobutyramide orthoester conjugate) refluxed in ethanol (30 ml) with cyclopropylamine (10 g) 2.5 hours. Evaporation left a syrup which was dissolved in 10% isopropanolchloroform (200 ml). This solution was stirred vigorously with saturated aqueous sodium bicarbonate (25 ml). The organic layer was separated and the aqueous layer washed with additional 10% isopropanolchloroform. The combined organic layers were dried (MgSO$_4$). Evaporation left a pale yellow glass (2.4 g) which was chromatographed on silica gel. The title compound was eluted with 2–3% methanol-ethyl acetate as a white solid (1.02 g, 53%); recrystallisation of such a sample from methanol-acetonitrile gave the title compound as white needles; mp. 197.5°–198°.

$^1$H-NMR (DMSO-d$_6$) δ 9.75 (s, 1, NHCO) 7.93 (s, 1, purine H-8), 7.82 (br s, 1, NH-cyclopropyl), 6.12 and 5.92 m, 2, CH=CH), 5.50 (m, 1, CH-N, 4.73 (t, J=5.3, 1, OH), 3.46 (m, 2, CH$_2$-O), 3.25–3.00 (m, 2, CHMe$_2$ and CH), 2.91 (m, 1, CH), 2.75–2.6 (m, 1, 0.5 CH$_2$), 1.7–1.6 (m, 1, 0.5 CH$_2$), 1.07 (d, J=6.8, 6, CHMe$_2$), 0.75–0.6 (m, 4, 2 cyclopropyl, CH$_2$); [α]$_D^{20}$−70.7°, [α]$_{436}^{20}$−159.0° (c=1.02, MeOH).

Anal Calcd. for C$_{18}$H$_{24}$N$_6$O$_2$: Calcd.: C, 60.66; H, 6.79; N, 23.58. Found: C, 60.62; H, 6.83; N, 23.51.

Continued elution of the column with 5% methanol-ethyl acetate gave additional title compound contaminated by ca. 10% of (−)-(1S,4R)-cis-4-[2-amino-6-(cyclopropylamino)-9H-purin-9-yl]-2-cyclopentene-1-methanol as a pale yellow solid foam (928 mg).

EXAMPLE 28

(−)-(1S,4R)-cis-4-[2-Amino-6-(cyclopropylamino)-9H-purin-9-yl]-2-cyclopentene-1-methanol (−)-(1R,4S)-cis-N-[6-(cyclopropylamino)-9-(4-hydroxymethyl)-2-cyclopentene-1-yl)-9H-purin-2-yl]isobutyramide (1.33 g, 3.73 mmol) prepared as described in Example 27, was stirred with 1N hydrochloric acid (40 ml) for 2 days at ambient temperature. The pH was adjusted to 7.0 with sodium hydroxide and the mixture evaporated to dryness. The residual solids were triturated with hot EtOH (3×25 ml). The ethanol was evaporated to leave yellow glass which was chromagraphed on silica gel. The title compound was eluted with 3% methanol-ethyl acetate as a colourless solid foam (857 mg, 80%), $^1$H-NMR and [α]$_D^{20}$, identical with that of the title compound of Example 19.

EXAMPLE 29

(−)-(1S, 4R)-cis-4-2-Amino-6-(cyclopropylamino)-9H-purin-9-yl]-2-cyclopentene-1-methanol hydrochloride.

(−)-(1S, 4R)-cis-[2-Amino-6-(cyclopropylamino)-9H-purin-9-yl]-2-cyclopentene-1-methanol (1.90 g, ca. 6.3 mmol by $^1$H-NMR) was dissolved in 1N hydrochloric acid (7.0 ml) and ethanol. The solution was evaporated to dryness and the residue redissolved in ethanol (15 ml). Ethyl acetate was added slowly, to a total volume of 80 ml. The off-white powder which formed was filtered off and dried under vacuum to give the title compound (2.07 g, 97%); mp. collapses at 125°–130°, dec. above 138° C., [α]$_{589}^{20}$−27.1°, [α]$_{436}^{20}$−52.3° (c=0.199, MeOH).

Anal. Calcd. for C$_{14}$H$_{18}$N$_6$O.HCl.0.8H$_2$O: Calcd.: C. 49.87; H, 6.16; N, 24.92; Cl, 10.51. Found: C, 49.91; H, 6.16; N, 24.95; Cl, 10.52.

EXAMPLE 30

(−)-(1S,4)-cis-4-[2-Amino-6-(cyclopropylamino)-9H-purin-9-yl]-2-cyclopentene-1-methanol Dihydrochloride.

(−)-(1S,4R)-cis-4-[2-Amino-6-(cyclopropylamino)-9H-purin-9-yl]-2-cyclopentene-1-methanol (857 mg, 3.00 mmol) was dissolved in ethanolethyl acetate and 1N ethereal hydrochloric acid (12 ml) was added. The fine white precipitate was washed with ethyl acetate and dried under vacuum to give the title compound (642 mg, 75%); mp. 176°–180° dec.

Anal. Calcd. for C$_{14}$H$_{18}$N$_6$O.2HCl: Calcd.: C, 46.81; H, 5.61; N, 23.39; Cl, 19.74, Found: C, 46.82; H, 5.64; N, 23.33; Cl, 19.67.

EXAMPLE 31

(1R,4S)-4-(2-Amino-6-(cyclopropylamino)-9H-purin-9-yl)-2-cyclopentene-1-methanol O-diphosphate (+)-(1R,4S)-4-(2-Amino-6-(cyclopropylamino)-9H-purin-9-yl)-2-cyclopentene-1-methanol O-monophosphate, prepared as described in Example 9, was converted to the triethylammonium salt by taking a solution containing 0.5 mmol of the monophosphate as the ammonium salt, combining it with 10 ml of 0.5M triethylammonium bicarbonate and drying in vacuo, followed by another addition of 10 ml of 0.5M triethylammonium bicarbonate, then drying. Then, three times, 10 ml of acetonitrile were added and dried in vacuo. This was dissolved in 10 ml of 1,3-dimethyl-3,4,5,6-tetrahydro-2(1H)-pyrimidinone (Aldrich) then 0.43 g of 1,1'-carbonyl diimidazole (Aldrich, 2.6 mmol) was added and stirred for 2 hours at room temperature. Methanol (0.18 ml, 4.5 mmol) was added and stirred for 30 minutes. Tributylammonium pyrophosphate (Sigma, 1.2 g, 2.6 mmol) was added, stirred for 18 hours at room temperature, then 1 g of additional tributylammonium pyrophosphate (2.2 mmol) was added and stirred 8 hours at 40° C., then 50 ml of water was added. Both O-diphosphate and O-triphosphate were formed since the tributylammonium pyrophosphate contained orthophosphate impurity.

The reaction products were separated by DEAE Sephadex ion exchange chromatography in a 2.5×18 cm column of DEAE Sephadex A25 (Pharmacia) which had been equilibrated with 50 mM of ammonium bicarbonate (ABC). The column was washed with 1 l of 50 mM ABC then with a 2 l linear gradient of 50 to 800 mM ABC to elute the title compound followed by triphosphate, as described in more detail in Example 32. The fractions containing diphosphate were combined, dried in vacuo, redissolved in water then dried again to yield the ammonium salt of the title compound (0.077 mmol, 15% yield). UV scan: in 0.1M HCl λ max=254 and 298 nm; at pH 7 λ max=259 and 284 nm: in 0.1M NaOH λ max=259 and 284 nm.

An aliquot of diphosphate was treated with alkaline phosphatase (calf intestine, Boehringer Mannheim), sampled at various times and developed on thin layer chromatography (PEI- cellulose, Brinkman, 1M LiCl/1M formic acid 1:1). A sequential conversion of diphosphate to monophosphate to nucleoside was observed. The final amount of - phosphate released was determined by the method of Bencini (Bencini, D. A., Wild, J. R., and O'Donovan, G. A. Analytical Biochemistry 132:254–258(1983)) and the base/phosphate ratio was determined to be 1.0/11.5, indicating the presence of inorganic phosphate. UV purity was 99.8% on analytical HPLC (strong anion exchange column eluted with a gradient of 10 mM to 1M ammonium phosphate, pH 5.5).

EXAMPLE 32

(+)-(1R,4S)-4-(2-Amino-6-(cyclopropylamino)-9H-purin-9-yl)-2-cyclopentene-1-methanol O-triphosphate Continued elution of the column described in Example 31 gave, on evaporation, the ammonium salt of the title compound. This salt was converted to the sodium salt by passage through a Dowex AG 50W-X8 (Bio-Rad) resin column (sodium form, 20 ml). The fractions containing nucleotide were concentrated in vacuo to yield 0.31 mmol (61%). UV scan: in 0.1M HCl λmax=254 and 299 nm; at pH 7 λmax=259 and 284 nm: in 0.1M NaOH λmax=259 and 284 nm. Optical rotation in water at 3.83 g/100 ml was $[\alpha]20= +43.2°$ at 589 nm. UV purity was 99.1% on analytical HPLC (strong anion exchange column eluted with a gradient of 10 mM to 1M ammonium phosphate, ph 5.5) with 0.9% diphosphate present. An aliquot of triphosphate was treated with alkaline phosphatase (calf intestine, Boehringer Mannheim), sampled at various times and developed on thin layer chromatography (PEI-cellulose, Brinkman, 1M LiCl/1M formic acid 1:1). A sequential conversion of triphosphate to diphosphate to monophosphate to nucleoside was observed. The final amount of phosphate released was determined by the method of Bencini (Bencini, D. A., Wild, J. R., and O'Donovan, G. A. Analytical Biochemistry 132:254–258 (1983)) and the base/phosphate ratio was determined to be 1.0/2.7.

EXAMPLE 33

(1S,4R)-4-(2-Amino-6-(cyclopropylamino)-9H-purin-9-yl)-2-cyclopentene-1-methanol O-diphosphate The (−)-(1S,4R)-4-(2-Amino-6-(cyclopropylamino)-9H-purin-9-yl)-2-cyclopentene-1-methanol O-monophosphate, prepared as described in Example 8, was converted to the triethylammonium salt by taking a solution containing 0.49 mmol of the monophosphate as the ammonium salt, combining with 5 ml of 0.5M triethylammonium bicarbonate and drying in vacuo, followed by another 5 ml of 0.5M triethylammonium bicarbonate then repeating twice. Then, three times, 5 ml of acetonitrile were added and dried in vacuo. This was dissolved in 7 ml of 1,3-dimethyl-3,4,5,6-tetrahydro-2(1H)-pyrimidinone (Aldrich) then 0.39 g of 1,1'-carbonyl diimidazole (Aldrich, 2.4 mmol) was added and stirred for 30 minutes at room temperature. Methanol (0.16 ml, 4.0 mmol) was added stirred for 30 minutes. Tributylammonium pyrophosphate (made by exchanging the salt of tetrasodium pyrophosphate for hydrogen on an ion-exchange resin, then neutralizing with tributylamine and drying, 2.4 mmol) was added, stirred for 18 hours at room temperature, then 50 ml of water was added. Both O-diphosphate and O-triphosphate were formed since the tributylammonium pyrophosphate contained orthophosphate impurity.

The reaction products were separated by DEAE Sephadex ion exchange chromatography in a 2.5×18 cm column of DEAE Sephades A25 (Pharmacia) which had been equilibrated with 50 mM ammonium bicarbonate (ABC). The column was washed with 1 L of 100 mM ABC then with a 2 L linear gradient of 100 to 800 mM ABC to elute the to elute the title compound followed by the triphosphate as described in more detail in Example 34. The fractions containing disphosphate were combined, dried in vacuo, redissolved in water then repeated twice to yield the ammonium salt of the title compound (0.032 mmol, 6% yield). UV scan: in 0.1M HCl λmax=254 and 298 nm; at pH 7 λmax=259 and 284 nm: in 0.1M NaOH λmax=258 and 284 nm.

An aliquot of triphosphate was treated with alkaline phosphatase (calf intestine, Boehringer Mannheim), sampled at various times and developed on thin layer chromatography (PEI-cellulose, Brinkman, 1M LiCl/1M formic acid 1:1). A sequential conversion of diphosphate to monophosphate to nucleoside was observed. The final amount of phosphate released was determined by the method of Bencini (Bencini, D. A., Wild, J. R., and O'Donovan, G. A. Analytical Biochemistry 132:254–258 (1983)) and the base/phosphate ratio was determined to be 1.0/4.7, indicating the presence of inorganic phosphate. UV purity was 97% on analytical HPLC (strong anion exchange column eluted with a gradient of 10 mM to 1M ammonium phosphate, pH 5.5).

EXAMPLE 34

(1S,4R)-4-(2-amino-6-(cyclopropylamino)-9H-purin-9-yl)-2-cyclopentene-1-methanol O-triphosphate Continued elution of the column described in Example 33 gave, on evaporation, the ammonium salt of the title compound. This salt was converted to the sodium salt by passage through a Dowex AG 50W-X8 (Bio-Rad) resin column (sodium form, 20 ml). The fractions containing nucleotide were concentrated in vacuo to yield 0.4 mmol (81%). UV scan: in 0.1M HCl λmax=254 and 299 nm; at pH 7 λmax=259 and 284 nm: in 0.1M NaOH λmax=259 and 284 nm. Optical rotation in water at 6.14 g/100 ml was $[\alpha]20= -47.1°$ at 589 nm. UV purity was 99.5% on analytical HPLC (strong anion exchange column eluted with a gradient of 10 mM to 1M ammonium phosphate, ph 5.5) with 0.5% diphosphate present. An aliquot of triphosphate was treated with alkaline phosphatase (calf intestine, Boehringer Mannheim), sampled at various times and developed on thin layer chromatography (PEI-cellulose, Brinkman, 1M LiCl/1M formic acid 1:1). A sequential conversion of triphosphate to diphosphate to monophosphate to nucleoside was observed. The final amount of phosphate released was determined by the method of Bencini (Bencini, D. A., Wild, J. R., and O'Donovan, G. A. Analytical Biochemistry 132:254–258 (1983)) and the base/phosphate ratio was determined to be 1.0/2.8.

EXAMPLE 35

(1S,4R)-4-[2-Amino-6-(cyclopropylmethylamino)-9H-purin-9-yl]-2-cyclopentene-1-methanol (1S,4R)-4-(2-Amino-6-chloro-9H-purin-9-yl)-2-cyclopentene-1-methanol (274 mg, 1.00 mmol), N-cyclopropyl-N-methylamine (0.71 g, 10 mmol), and absolute ethanol (6 mL). The residue was chromatographed on silica gel. The Title compound was eluted with 10% methanol-chloroform as a colorless glass. Evaporation of an ethanol solution and drying with phosphorus pentoxide at 0.2 mm Hg gave the title compound as a white solid foam (293 mg, 98%); $^1$H-NMR and $[\alpha]^{20}$ 589 identical with those of the title compound of Example 11.

EXAMPLE A

Tablet Formulations

The following formulations A, B and C are prepared by wet granulation of the ingredients with a solution of povidone, followed by addition of magnesium stearate and compression.

Formulation A

| | | mg/tablet | mg/tablet |
|---|---|---|---|
| (a) | Active ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
| | | 500 | 300 |

Formulation B

| | | mg/tablet | mg/tablet |
|---|---|---|---|
| (a) | Active ingredient | 250 | 250 |
| (b) | Lactose | 150 | — |
| (c) | Avicel PH 101 | 60 | 26 |
| (d) | Povidone B.P. | 15 | 9 |
| (e) | Sodium Starch Glycollate | 20 | 12 |
| (f) | Magnesium Stearate | 5 | 3 |
| | | 500 | 300 |

Formulation C

| | mg/tablet |
|---|---|
| Active ingredient | 100 |
| Lactose | 200 |
| Starch | 50 |
| Povidone | 5 |
| Magnesium stearate | 4 |
| | 359 |

The following formulations, D and E, are prepared by direct compression of the admixed ingredients. The lactose in formulation E is of the direct compression type (Dairy Crest - "Zeparox").

Formulation D

| | mg/tablet |
|---|---|
| Active ingredient | 250 |
| Pregelatinised Starch NF15 | 150 |
| | 400 |

Formulation E

| | mg/tablet |
|---|---|
| Active ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

| | | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P. | 28 |
| (e) | Magnesium Stearate | 7 |
| | | 700 |

Drug release takes place over a period of about 6–8 hours and is complete after 12 hours.

EXAMPLE B

Capsule Formulations

Formulation A

A capsule formulation is prepared by admixing the ingredients of Formulation D in Example A above and filling into a two-part hard gelatin capsule. Formulation B (infra) is prepared in a similar manner.

Formulation B

| | | mg/capsule |
|---|---|---|
| (a) | Active ingredient | 250 |
| (b) | Lactose B.P. | 143 |
| (c) | Sodium Starch Glycollate | 25 |
| (d) | Magnesium Stearate | 2 |
| | | 420 |

Formulation C

| | | mg/capsule |
|---|---|---|
| (a) | Active ingredient | 250 |
| (b) | Macrogol 4000 B.P. | 350 |
| | | 600 |

Capsules of formulation C are prepared by melting the Macrogol 4000 BP, dispersion the active ingredient in the melt and filling the melt into a two-part hard gelatin capsule.

Formulation D

|  | mg/capsule |
| --- | --- |
| Active ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

|  |  | mg/capsule |
| --- | --- | --- |
| (a) | Active ingredient | 250 |
| (b) | Microcrystalline Cellulose | 125 |
| (c) | Lactose B.P. | 125 |
| (d) | Ethyl Cellulose | 13 |
|  |  | 513 |

EXAMPLE C

Injection Formulation

Formulation A

| Active ingredient | 0.200 g |
| --- | --- |
| Hydrochloric acid solution, 0.1M, or Sodium hydroxide solution, 0.1M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

Formulation B

| Active ingredient | 0.125 g |
| --- | --- |
| Sterile, pyrogen-free, pH 7 phosphate buffer q.s. to | 25 ml |

EXAMPLE D

Intramuscular Injection

| Active ingredient | 0.20 g |
| --- | --- |
| Benzyl Alcohol | 0.10 g |
| Glycofurol 75 | 1.45 g |
| Water for Injection | q.s. to 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE E

Syrup

| Active ingredient | 0.25 g |
| --- | --- |
| Sorbitol Solution | 1.50 g |
| Glycerol | 2.00 g |
| Sodium Benzoate | 0.005 g |
| Flavor, Peach 17.42.3169 | 0.0125 ml |
| Purified Water | q.s. to 5.00 ml |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

EXAMPLE F

Suppository

|  | mg/suppository |
| --- | --- |
| Active ingredient | 250 |
| Hard Fat, BP (Witepsol H15 - Dynamit NoBel) | 1770 |
|  | 2020 |

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE G

Pessaries

|  | mg/pessary |
| --- | --- |
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

Antiviral Activity a) Anti-HIV Activity (1S,4R)-cis-4-[2-amino-6-(cyclopropylamino)-9H-purin-9-yl]-2-cyclopentene-1-methanol was tested for anti-HIV activity in $MT_4$ cells according to the method described by Averett, D. R., *J. Virol. Methods*, 23 1989, 263–276 and was found to have an $IC_{50}$ value of 4.0±1.4 μM (average of 10 determinations).

b) Anti-HBV Activity

The human HBV producer cell line of HepG2,2.2.15, described and characterised by Sells et al., PNAS 84: 1005, 1987 and J. Virol. 62: 2836, 1988 has been shown to share many characteristics of the HBV chronically infected hepatocyte. It is infectious as demonstrated by the ability to cause disease in chimpanzees.

To test compounds for anti-HBV activity, monolayer cultures were treated with the test compound: 50-200 μM for ten days.

Supernatant media containing extracellular virion DNA (Dane particles) were harvested on days three, six and ten, treated with proteinase K (1 mg/mL) and sodium dodecyl sulfate (1%), and incubated at 50° C. for one hour. DNA was extracted with equal volumes of phenol followed by chloroform and then precipitated by ammonium acetate and propanol. The DNA precipitate was dissolved and collected on nitrocellulose using the procedure of Schleicher and Schuell (S&S, 10 Optical Ave., Kenne, N.H. 03431, Publication #700, 1987), and treated as described by Southern, J. Mol. Biol., 98, 503, 1975. Cells were harvested, and the intracellular DNA was obtained after cell lysis with guanidine isothiocyanate. The intracellular DNA was handled in the same manner as the extracellular DNA. After precipitation by ammonium acetate and propanol, the intracellular DNA precipitate was dissolved, cut by restriction endonuclease, Hind III, applied to agarose gel and then treated as described by Southern to determine the quantity of replicative intermediate forms. The antiviral effect of the drug was determined by measuring at least a 100-fold reduction of the amount of Dane particles extruded into the culture medium and a similar decrease in the intracellular replicative intermediates.

(1S,4R)-cis-4-[2-Amino-6-(N-cyclopropyl-N-methylamino)-9H-purin-9-yl]-2-cyclopentene-1-methanol was tested by the above procedure and found to have potent anti-HBV activity at 100 μM.

I claim:

1. Enantiomeric compounds of formula (III)

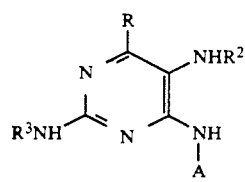

(III)

wherein A represents the 2-cyclopentene-1-methanol-4-yl group in either the (1S,4R) or (1R,4S) configuration, R represents a cyclopropylamino or N-cyclopropyl-N-methylamino group, $R^2$ represents hydrogen or a formyl group and $R^3$ represents a $C_{1-6}$alkanoyl group, or a salt or ester thereof.

2. Enantiomeric compounds of formula (V)

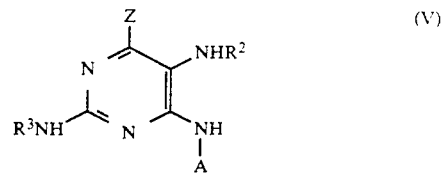

(V)

wherein A represents the 2-cyclopentene-1-methanol-4-yl group in either the (1S,4R) or (1R,4S) configuration, Z represents a halo group, $R^2$ represents hydrogen or a formyl group and $R^3$ represents a $C_{1-6}$alkanoyl group, or a salt or ester thereof.

3. (1R,4S)-cis-N-[4-Chloro-5-formamido-6-((4-(hydroxymethyl)-2-cyclopentene-1-yl)amino)-2-pyrimidinyl]isobutyramide substantially free of the corresponding (1S,4R) enantiomer.

4. Compounds of formula (VII)

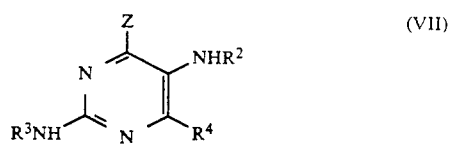

(VII)

wherein Z represents a halo group, $R^2$ represents hydrogen or a formyl group, $R^3$ represents a $C_{1-6}$alkanoyl group and $R^4$ represents a halo group, or a salt thereof.

5. N-(4,6-Dichloro-5-formamido-2-pyrimidinyl)isobutyramide.

6. Compounds of formula (IX)

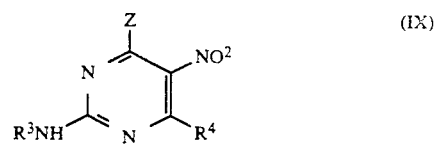

(IX)

wherein Z represents a halo group, $R^3$ represents a $C_{1-6}$alkanoyl group and $R^4$ represents a halo group or a salt thereof.

7. N-(4,6-Dichloro-5-nitro-2-pyrimidinyl)isobutyramide.

8. Compounds of formula (X)

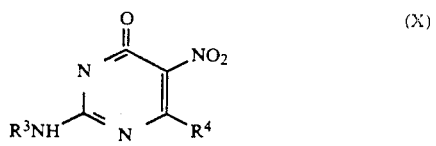

(X)

wherein $R^3$ represents a $C_{1-6}$alkanoyl group and $R^4$ represents a halo group or a salt thereof.

9. N-(4-Chloro-1,6-dihydro-5-nitro-6-oxo-2-pyrimidinyl)isobutyramide.

* * * * *